United States Patent [19]
Pierfitte

[11] Patent Number: 5,367,169
[45] Date of Patent: Nov. 22, 1994

[54] GAMMA CAMERA WITH TWO OPPOSITE DETECTORS HAVING INDEPENDENT RADIAL MOVEMENTS

[75] Inventor: Michel Pierfitte, Villepreux, France

[73] Assignee: SOPHA Medical, Paris, France

[21] Appl. No.: 894,026

[22] Filed: Jun. 4, 1992

[30] Foreign Application Priority Data

Jun. 7, 1991 [FR] France .................................. 91 06961

[51] Int. Cl.⁵ .............................................. G01T 1/166
[52] U.S. Cl. ............................ 250/363.05; 250/363.04; 250/363.08
[58] Field of Search ...................... 250/363.05, 363.08, 250/363.04

[56] References Cited

U.S. PATENT DOCUMENTS

| | | | |
|---|---|---|---|
| H12 | 1/1986 | Bennett et al. | 250/363.09 |
| 4,476,389 | 10/1984 | Ueyama et al. | 250/363.05 |
| 4,649,277 | 3/1987 | Terra et al. | 250/363.05 |
| 4,652,759 | 3/1987 | Platz | 250/363.05 |
| 4,692,625 | 9/1987 | Hanz et al. | 250/363.08 |
| 5,093,575 | 3/1992 | Perusek | 250/363.08 |

FOREIGN PATENT DOCUMENTS

| | | |
|---|---|---|
| 0266846 | 5/1988 | European Pat. Off. . |
| 0332937 | 9/1989 | European Pat. Off. . |
| 3145430 | 5/1983 | Germany . |
| 57-53673 | 3/1982 | Japan .............. 250/363.04 |
| 58-92975 | 6/1983 | Japan .............. 250/363.04 |
| 60-128383 | 7/1985 | Japan .............. 250/363.08 |

*Primary Examiner*—Constantine Hannaher
*Attorney, Agent, or Firm*—Robert Groover

[57] ABSTRACT

Improvements are made in the movements of a gamma camera, especially a gamma camera provided with two detector heads, by supporting each of these detector heads with a stirrup provided with two flanks. A bearing can slide within each of the flanks. This bearing holds a pin for the angulation and holding of the detector head. Each detector head can thus be shifted in translation independently, when the two bearings shift together and in the same direction in the flanks. It can furthermore accept a movement of angulation when it is rotated on itself, even about these axes. It is shown that this device improves the ergonomy of use and that it furthermore enables better-quality imaging.

20 Claims, 2 Drawing Sheets

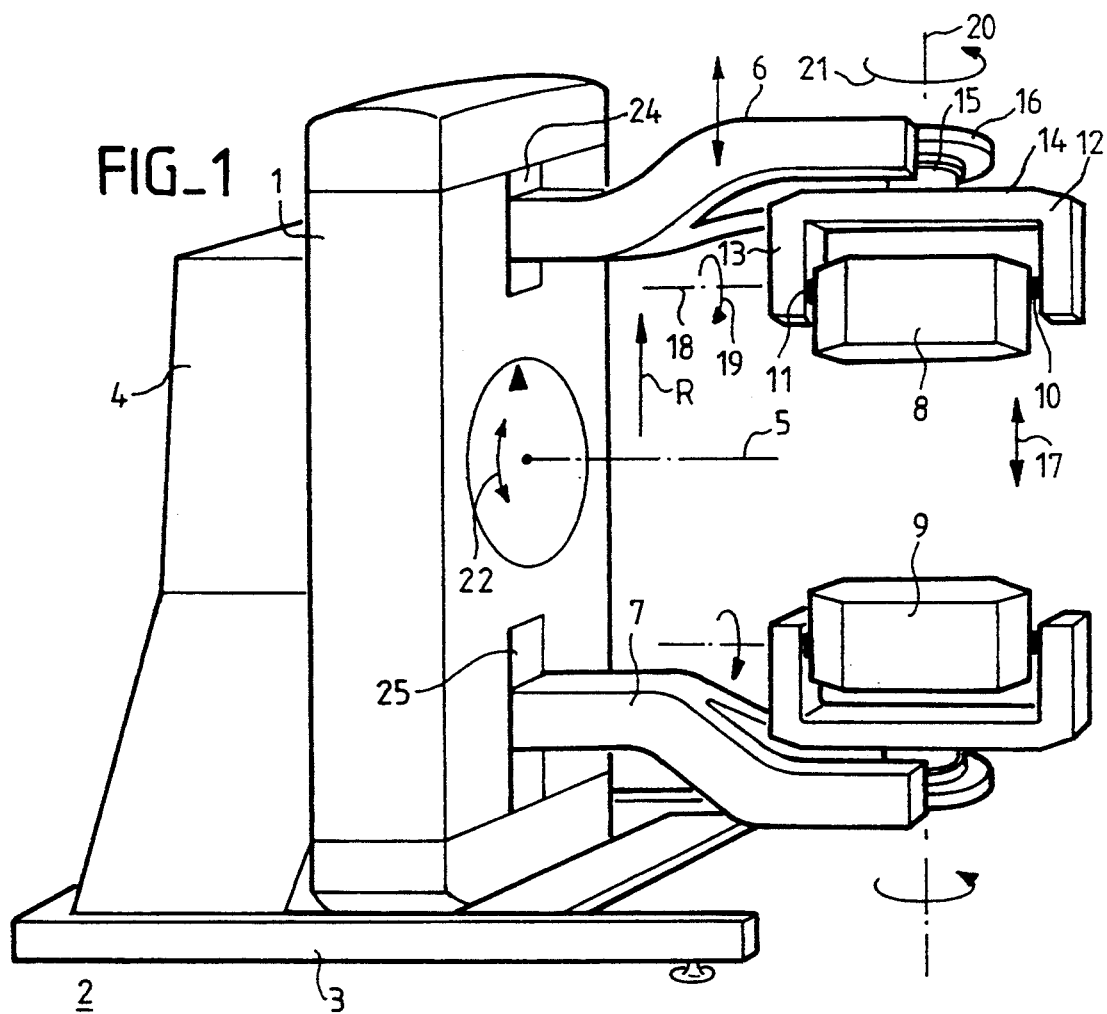
FIG_1
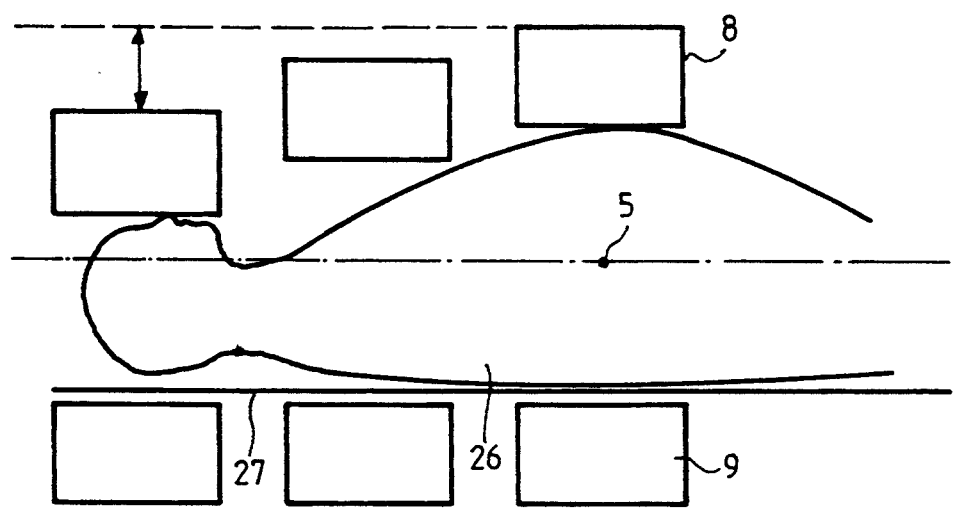
FIG_2

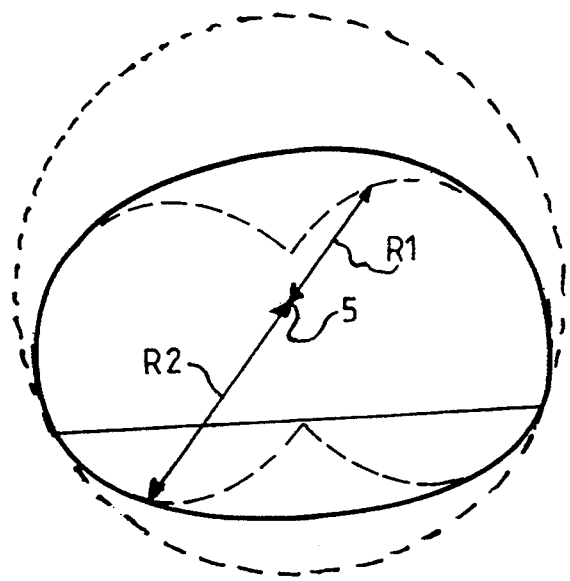
FIG_3
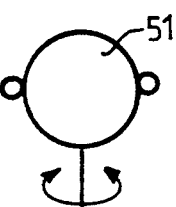
FIG_4

GAMMA CAMERA WITH TWO OPPOSITE DETECTORS HAVING INDEPENDENT RADIAL MOVEMENTS

BACKGROUND OF THE INVENTION

1. Field of the Invention

An object of the present invention is a gamma camera, preferably with two opposite detectors having independent radial movements. In this camera, the ergonomy of use as well as the efficiency of detection are improved, since the detectors are maintained independently, at the smallest possible distance from the patient to be examined, thus increasing the resolution.

2. Description of the Prior Art

Gamma cameras are described, for example, in the U.S. patent by Anger, U.S. Pat. No. 3,011,057. A gamma camera is an apparatus comprising a stand, which is fixed or rotating or even movable with respect to the ground and carries a detector, also called a detector head, at the end of an arm. This detector is provided with an array of photomultiplier tubes, the input faces of which are juxtaposed with one another and constitute the detection surface of the detector head and its detection field.

The following is the principle of the examination. A radioactive substance is injected into a patient to be examined. This substance is thallium for example. The radioactive emission excites a scintillator crystal of the detector which converts the energy of the gamma photons into a light energy that can be detected by the photomultiplier tubes. The scintillator crystal is preceded by a collimator.

The scintillations emitted are detected by the photomultiplier tubes which produce electrical signals depending on the light intensity received. By carrying out barycentric tracking operations on all these electrical signals, it is possible, in a known way, to determine the localization X Y of the origin of the scintillation in the detection field. An incremental acquisition is then carried out by totalizing the number of scintillations (or strokes) detected per localization element called a pixel.

By leaving the detector head in a given position for a certain time above the examined body, it is then possible, for a given angle of sight, called a projection, to obtain an image that reveals the concentration of the emitting substance in the body. A tomographic examination consists in acquiring one image per angle of sight, for a large number of angles of sight, evenly spaced out on an angular sector of at least 180°. It is then possible, with computation algorithms, notably filtered back projection, to reconstitute the image of a volume of the body.

To increase the sensitivity of the camera, the common practice has been to use a stand, capable of rotating if necessary and provided with two detector head instead of only one. These two heads face each other. When they rotate, the heads rotate together about the patient being examined.

The stand is normally capable of making a rotation on itself about a tomographic axis of rotation. The detector head is held by an arm fixed to the stand by a mechanism of radial movement. The arm that supports the head describes a cylinder in the course of the rotation. In principle, the detector head is oriented so that the normal to its detector field, in the center of this field, is perpendicular to the rotation axis of the stand. When a radial movement is carried out, the arm is moved away or brought closer to this rotation axis. When the gamma camera concerned is one with two detector heads, each of these heads is mounted on an arm. The two arms are fixed symmetrically to the stand, on either side of the rotation axis. Besides, they are shifted symmetrically about this axis, both in rotation and in radial movement.

In a tomographic examination, the two heads rotate about the patient and the value of the radius, for each angle of rotation, should be chosen in such a way that none of the detectors comes into contact with the patient. The two radii of spacing of the heads are identical. Since the patient has no symmetry of revolution, there is always one detector that is further away from the patient than the other one. For this detector which is further away, there is a loss of resolution. The resolution is poorer than if this detector were to be as close as possible to the patient.

Furthermore, when the examination covers the whole body, the patient is placed on a bed and the stand bearing the two facing detectors is driven by a lateral movement. Given the symmetrical radial movement of the above-mentioned heads, it being known, firstly, that the lower head should keep an altitude, or a radius value, that is constant to change position at a fixed distance from the bed and, furthermore, it being known that the upper head should provide a passage for the patient's most prominent parts (generally his belly), it is necessary to fix the value of the radius throughout the lateral movement, thus penalizing the resolution of the upper head.

SUMMARY OF THE INVENTION

It is an object of the invention to overcome these drawbacks by enabling independent movements for each of the detectors. This independence is provided by a telescopic radial movement of each of the detectors.

An object of the invention, therefore, is a gamma camera comprising a rotating stand bearing an arm to hold a detector placed at the end of this arm, said arm being radially movable with respect to the rotation axis of the stand, wherein this stand comprises means of telescopic movement to prompt a translation of the head perpendicularly to the arm.

When there are two heads, the telescopic movements of these two heads can also be independent.

Another object of the invention is a gamma camera comprising a stand, two detector heads, and two holding arms fixed by one of their ends to the stand and by the other end to this head wherein the arms have, at their ends fixed to the heads, means of telescopic movement to prompt independent translations of these heads perpendicularly to the arms.

According to one disclosed embodiment, the heads define respective rectangular detection fields, and the arms include means to orient a substantial portion of the fields of the heads in any direction within a plane perpendicular to the direction of translational movement.

BRIEF DESCRIPTION OF THE DRAWINGS

The invention shall be understood more clearly from the following description and from the accompanying figures which are given purely by way of an indication and in no way restrict the scope of the invention. Of these figures:

FIG. 1 shows a view in perspective of a gamma camera according to the invention;

FIG. 2 shows a mode of use of the gamma camera of the invention wherein the facilities of telescopic movement are exploited;

FIG. 3 shows a schematic view of a tomographic mode of exploration in which the telescopic movement is exploited;

FIG. 4 is a detail showing the telescopic movement.

MORE DETAILED DESCRIPTION

FIG. 1 shows a gamma camera according to the invention. This gamma camera has a rotating stand 1 supported by a under-frame 2 which comprises a footing 3 holding a supporting frame 4. The supporting frame 4 comprises a shaft (not shown) enabling the rotating stand 1 to rotate about an axis 5 that is substantially horizontal. There are two arms, 6 and 7 respectively, and each holds a detector head, 8 and 9 respectively, at its end. The two heads are held at the end of their arms in the same way. For example, the head 8 is provided with two pins 10 and 11 which may rotate in bearings in holding the head. These bearings, themselves, are held in flanks, 12 and 13 respectively, of a stirrup 14. The tip of the stirrup 14 is connected to a ring 15 which can rotate inside a concentric ring 16 which is itself fixed to the end of the arm 6.

An angular rotation or "angulation" movement of the head, effected about an axis 18 which goes through the pins and the bearings, is represented by the arrow 19. In a simplified version, this movement is achieved manually. These angulation movements are achieved manually with the possibility of selection among pre-defined positions. In one example, these pre-defined positions are constituted by notches made on the periphery of circular plates concentric to the axis of angulation and fixedly joined to each of the heads. Two catches may get engaged in these notches and may thus keep the angulation of the heads in pre-defined positions.

The rotating stand assembly can rotate about the axis 5 in a rotational movement 22. The distance R between the axis 5 and the arm ss called the radius. The radial movement is the one that causes variation in the value of this radius. The latter movement is already known.

The stirrup 14, which has an inverted U shape, includes a sliding saddle in each of its flanks 12 and 14, as can be seen in FIG. 4, to enable the bearings 50, which hold the pins 10 and 11, to move vertically. This movement is preferably motor-driven by a motor placed in each stirrup. The motors are independent. The motor 51 is placed, for example, at the center of the stirrup 14. It drives two worm screws by means of two belts 52 and 53. Only the worm screw 54 is shown. The worm screw 54 is screwed into a nut 55 that is fixedly joined to a saddle 56. The saddle 56 is provided with two sleeves 57 and 58 which slide along two shafts 59 and 60. The shafts 59 and 60 are held in a position where they are fixedly joined to the flanks of the stirrup. The head of the screw 54 is kept fixed in translation but is rotationally free in this stirrup. The telescopic movement is shown symbolically by the double-headed arrow 17 in FIG. 1.

FIG. 2 shows an example of an examination in which a patient 26 is lying on a bed 27. The two heads 8 and 9 are shown, in a standard way, on either side of the middle 5 of the rotating stand. When the bed 27 is shifted relatively towards the right or left of the heads, the patient moves between the two heads: it is possible to carry out a full-body examination. During this examination, a permanent acquisition is made. As and when the patient's trunk passes beneath the head 8 and it becomes possible to examine his head, the telescopic movement 17 is used to prompt the descent of the upper detector head 8 so as make this detector head approach the patient's head as closely as possible. In practice, the telescopic movement that can be achieved is of the order of 8 cm. In the position shown to the left of FIG. 2, the upper head 8 is in the position closest to the patient's head: the resolution in detection is improved.

FIG. 3 shows a schematic view of a tomographic examination of a patient (not shown). In this case, while the bed is substantially parallel to the axis 5, the gamma camera is made to rotate about the patient's body. For each projection, then, the faculties of telescopic projection are used to bring each head as close as possible to the body in taking account of the space occupied by the patient and the bed and of the constant center geometric exploration that must be adhered to. With the invention, an improved resolution is obtained since the heads may be brought closer to the body. The solid line contour represents the ideal trajectory for which the most efficient use is made, with the invention, of the faculties of independent telescopic movement, with R1 different from R2. The trajectories in dashes show the room for adjustment of these telescopic movements. The solid line is contained between the two dashed lines.

What is claimed is:

1. A gamma camera comprising
   a rotating stand bearing two detector heads mounted on two respective holding arms that are radially movable with respect to a rotation axis of said stand,
   said arms comprising a translational means mounted and connected to provide independent translations of said heads perpendicularly to said arms.

2. A gamma camera according to claim 1, wherein said means of translational movement comprises means to carry out an angulation of the heads.

3. A gamma camera according to claim 2, wherein said means of translational movement comprises stirrups provided with two flanks, said stirrups having heads fixed to the ends of said arms, said flanks comprising rotating bearings to hold said detector heads in angulation.

4. A gamma camera according to claim 1, wherein said translational means comprises a stirrup provided with two flanks, said stirrup comprising a head which is fixed to the end of said arm, said flanks comprising bearings that are movable along said flanks to enable the movement of said detector heads.

5. A gamma camera according to claim 1, wherein said heads define respective rectangular detection fields and wherein said arms have means to orient a substantial portion of the fields of said heads in any direction within a plane perpendicular to the direction of translational movement.

6. A gamma camera comprising
   a stand, two detector heads, and two holding arms,
   each said arm having one end thereof mounted to said stand and another end thereof connected to a respective one of said heads;
   wherein one or both of said arms have, at their ends connected to said heads, means of translational movement to provide independent translation of said head perpendicularly to said arm, wherein said means of translational movement comprises means to carry out an angulation of the detector head and wherein said means of translational movement comprises stirrups provided with two flanks, said stirrups having heads fixed to the ends of said arms, said flanks comprising rotating bearings to hold said detector heads in angulation.

7. A gamma camera comprising
a stand, two detector heads, and two holding arms,
each said arm having one end thereof mounted to said stand and another end thereof connected to a respective one of said heads;
wherein one or both of said arms have, at their ends connected to said heads, means of translational movement to provide independent translation of said head perpendicularly to said arm, wherein said means of translational movement comprises a stirrup provided with two flanks, said stirrup comprising a head which is fixed to the end of said arm, said flanks comprising bearings that are movable along said flanks to enable the movement of said detector heads.

8. A gamma camera comprising
a stand, two detector heads, and two holding arms,
each said arm having one end thereof mounted to said stand and another end thereof connected to a respective one of said heads;
wherein one or both of said arms have, at their ends connected to said heads, means of translational movement to provide independent translation of said head perpendicularly to said arm, wherein said heads define respective rectangular detection fields and wherein said arms have means to orient a substantial portion of the fields of said heads in any direction within a plane perpendicular to the direction of translational movement.

9. A gamma camera comprising:
a rotating stand bearing two arms, said arms being each borne at a first end thereof by said stand, said arms being together radially movable with respect to a rotation shaft of said stand;
each of said arms holding by means of an intermediary piece a detector head placed at a second end of said arm;
said intermediary pieces holding said heads each by an angulation axis, said intermediary pieces being slidable with regard to said second end of said arms for translating said detector heads, independently of each other, perpendicularly with respect to said arms;
said angulation axis comprising means for blocking undesired tilts of said heads.

10. A gamma camera according to claim 9, wherein said detector heads have rectangular detection fields and wherein the arms have means to orient a big length of the fields of these detector heads in any direction contained in a plane perpendicular to the direction of sliding movement.

11. A gamma camera according to claim 9, wherein said intermediary pieces comprise stirrups each provided with two flanks and heads, said heads of said stirrups being fixed to said second end of said arms by orientating means, said flanks comprising rotating bearings to hold the detector heads in angulation.

12. A gamma camera according to claim 11, wherein said detector heads have rectangular detection fields and wherein the arms have means to orient a big length of the fields of these detector heads in any direction contained in a plane perpendicular to the direction of sliding movement.

13. A gamma camera according to claim 11, wherein said intermediary pieces comprise stirrups provided with two flanks, heads of said stirrups being fixed to said second end of said arms, said flanks comprising bearings that are movable along these flanks to enable said sliding movement of said detector heads.

14. A gamma camera according to claim 13, wherein said detector heads have rectangular detection fields and wherein the arms have means to orient a big length of the fields of these detector heads in any direction contained in a plane perpendicular to the direction of sliding movement.

15. A gamma camera according to claim 9, wherein said intermediary pieces comprise stirrups provided with two flanks, heads of said stirrups being fixed to said second end of said arms, said flanks comprising bearings that are movable along these flanks to enable said sliding movement of said detector heads.

16. A gamma camera according to claim 15, wherein said detector heads have rectangular detection fields and wherein the arms have means to orient a big length of the fields of these detector heads in any direction contained in a plane perpendicular to the direction of sliding movement.

17. A tomographic camera comprising:
first and second arms rotatable around a common axis which is substantially intermediate between said arms;
first and second detector heads each rotatably and tiltably mounted on a respective one of said arms;
said detector heads being translatable in a direction perpendicular to said common axis;
at least one of said detector heads being independently translatable in a direction perpendicular to said common axis.

18. The camera of claim 17, wherein said heads define respective rectangular detection fields.

19. A tomographic camera comprising:
a first mechanism mounted and configured to jointly support two arms in a jointly rotatable relationship about a first axis;
each said arm having a respective detector head movably mounted thereon;
a second mechanism mounted and configured, on at least one said arm, to provide controlled angulation of said detector heads away from said first axis; and
a third mechanism mounted and configured, on at least one said arm, to provide independent movement of said detector heads normal to said first axis, wherein said third mechanism comprises a stirrup provided with two flanks, said stirrup supporting a respective one of said heads, said flanks comprising bearings that are linearly movable along said flanks.

20. A method for tomographic scanning, comprising the steps of:
(a) providing a detection apparatus having first and second detection heads rotatable around a common axis of rotation which does not intersect either of said heads;
(b) introducing a patient body to at least partly intersect said common axis of rotation;
(c) providing relative motion between said patient body and said detection heads, to provide multiple views of said patient body by said detection heads; and
(d) during said step (c), independently translating said two heads toward or away from said common axis, to optimize resolution for each said detection head;
wherein said translating step (d) is implemented by linear movement of said head along flanks of a stirrup mounted to a respective arm, said stirrup supporting said head through bearings that are linearly movable along said flanks.

* * * * *